United States Patent [19]
Palmer et al.

[11] Patent Number: 5,475,165
[45] Date of Patent: Dec. 12, 1995

[54] TRIFLUOROMETHYLATION PROCESS

[75] Inventors: Keith W. Palmer, Landenberg, Pa.; Paul R. Resnick, Wilmington, Del.

[73] Assignee: E. I. Du Pont de Nemours and Company, Wilmington, Del.

[21] Appl. No.: 374,370

[22] Filed: Jan. 18, 1995

[51] Int. Cl.$^6$ .......... C07C 25/13; C07D 215/18; C07D 211/72; C07D 207/30

[52] U.S. Cl. .......... 570/144; 570/142; 549/29; 548/560; 546/180; 546/346

[58] Field of Search .......... 570/144, 142; 549/29; 548/560; 546/180, 346

[56] References Cited

U.S. PATENT DOCUMENTS

| | | | |
|---|---|---|---|
| 3,692,843 | 9/1972 | Resnick | 260/615 A |
| 4,808,748 | 2/1989 | Lin et al. | 570/144 |
| 4,814,480 | 3/1989 | Davidson | 570/144 |
| 4,814,482 | 3/1989 | Davidson | 570/144 |
| 4,822,904 | 4/1989 | Davidson | 570/144 |

FOREIGN PATENT DOCUMENTS 0139025  8/1982  Japan .......... 570/142

OTHER PUBLICATIONS

Qing–Yun Chen and Jian–Xing Duan, A Novel Trifluoromethylation Method of Saturated Organic Halides, *Tetrahedron Letters*, vol. 34, No. 26, pp. 4241–4244, 1993.

V. V. Berenblit et al., Polyfluoroacyl Fluorides Formed in the Electrochemical Fluorination of Methyl 3–Methoxypropionate, *Zhurnal Organicheskoi Khimii*, vol. 15, No. 2, pp. 284–292, Feb. 1979.

L. M. D'yachishina et al., Synthesis of Perfluoroalkyl Perfluorovinyl Ethers with Substituents in the Alkyl Group, *Zhurnal Organicheskoi Khimii*, vol. 8, No. 9, pp. 1790–1793, Sep. 1972.

*Primary Examiner*—Alan Siegel

[57] ABSTRACT

Aryl halide, such as idodobenzene, is reacted with perfluoromethoxycarboxylate, such as $CF_3OCF_2CO_2K$, in the presence of CuI and an inert aprotic polar solvent to obtain trifluoromethylaryl.

12 Claims, No Drawings

TRIFLUOROMETHYLATION PROCESS

FIELD OF THE INVENTION

This invention related to the trifluoromethylation of aromatic moieties.

BACKGROUND OF THE INVENTION

Chen, Q. Y. et. al., Tetrahedron Lett., 34, 4241–4244 discloses the desire to introduce the trifluoromethyl group into organic compounds, naming aryl, benzyl, vinyl, and allyl halides, for the purpose of producing compounds useful in medicine and biochemistry. This reference also discloses the use of methyl chloro- and bromo-difluoroacetate (Cl— or Br—$CF_2COOCH_3$) as trifluoromethylating agents for saturated alkyl halides in the presence of KF and a co-catalyst system wherein copper iodide and cadmium iodide are disclosed to be essential, such that if either one of the co-catalysts are omitted, no trifluoromethyl products were obtained.

Among the disadvantages of this process are the use of KF, which is difficult to dissolve in solvent useful in trifluoromethylation reaction and tends to produce unwanted byproducts and the requirement for the use of cadmium iodide, which is toxic.

SUMMARY OF THE INVENTION

The present invention is a trifluoromethylation process which avoids the need for either KF and cadmium iodide to provide trifluoromethylaryl reaction product. Specifically, the trifluoromethylation process of the present invention consists essentially of contacting and reacting aryl halide, which is aryl iodide or aryl bromide, with perfluoromethoxycarboxylate in the presence of cuprous iodide in an inert aprotic polar solvent and obtaining as a result thereof trifluoromethylaryl.

DETAILED DESCRIPTION

The perfluoromethoxycarboxylate is the trifluoromethylating agent. Preferred carboxylates have the formula $CF_3O(CF_2O)_nCF_2COOM$, wherein n is 0 or an integer of 1 to 10, and M is $CH_3$, quaternary ammonium, or metal, which is preferred. Methods of making the acyl fluoride of these carboxylates are disclosed in U.S. Pat. No. 3,692,843. These acyl fluorides can be converted to carboxylates by methods well known in the art. A carboxylic acid derivative is disclosed in EP 557167 A1, and the methyl and potassium salts are disclosed in Berenblit et al., Zh. Org. Khim.,15,284 (1979) and D'yachishina et. al., Zh. Org. Khim., 8, 1790(1972), respectively. The carboxylate may be obtained wherein n has a single value or multiple values, in which case, if desired, the mixture of compounds can be separated into fractions each having a single of n value. When available as the mixture, compounds in which n=1 to 5 will predominate. Examples of metal carboxylates are the alkali metal carboxylates, such as potassium and sodium, with potassium being preferred, and alkaline earth metal carboxylates, such as calcium and magnesium. The simplest quaternary ammonium carboxylate is ammonium carboxylate.

The preferred aryl halide is aryl iodide because of its greater reactivity in the process. Aryl iodide produces high yields of trifluoromethylaryl reaction product in reasonable periods of time. The aromatic moiety of the aryl halide is inert in the reaction and thus can have a wide variety of identities of simple or complex structures, including the benzene ring structure and condensed ring structures such as naphthalene and anthracene, and heterocyclic compounds which have aromatic character, such as thiophene, pyrrole, pyridine and quinoline. The aromatic moiety can be unsubstituted except for the halide substitutuent or substituted, provided any substituents other than the halide are inert in the reaction. The halide may be directly substituted onto the aromatic moiety as in the case of such halides as iodo- and bromo-benzene, iodo- or bromo-4-nitrobenzene, and 1-iodonaphthalene. The halide may also be indirectly substituted onto the aromatic moiety as in the case of such halides as benzyl bromide or iodide. The aryl halide should also be soluble in the solvent used in the reaction.

Examples of solvents which are inert, aprotic and polar, are N,N-dimethylformamide, which is preferred, N,N-dimethylacetamide, N-methyl pyrrolidone, hexamethyl phosphoric triamide and hexamethylphosporous triamide. These organic solvents are selected to have a boiling point which is greater than the temperature used for the conduct of the reaction. The reaction can be conducted at atmospheric pressure, but superatmospheric pressure can be used if desired, e.g., to keep the solvent in the liquid state at the reaction temperature.

The cuprous iodide (CuI) should be dry and free of contaminants for best results.

With respect to amounts of reactants, at least 0.8 mole of the carboxylate is preferably present for each mole of the halide and more preferably, at least a stoichiometric amount of the carboxylate. Excess carboxylate can also be present, e.g., up to two moles/mole of halide. At least 0.008 mole of cuprous iodide for each mole of halide is generally required to obtain the trifluoromethylaryl product. Preferably, at least 0.8 mole of cuprous iodide is present for each mole of the carboxylate and more preferably, at least a stoichiometric amount of cuprous iodide relative to the carboxylate reactant is present. Generally no benefit results by having more than 1.5 moles of the cuprous iodide per mole of the carboxylate.

The reaction is generally conducted by adding the reactants to the inert solvent in any particular order desired, followed by heating to dissolve all of the reactants, using stirring if necessary. The heating of the resultant solution to a temperature within the range of 50° C. to 200° C. will generally be sufficient to cause the reaction to occur. The preferred temperature range for the reaction is 80° C. to 130° C., and the more preferred temperature range is 100° C. to 120° C. The resultant trifluoromethylaryl can be separated from the reaction medium by known organic chemistry techniques, such as distillation, extraction, or crystallization, depending on the particular trifluoromethylaryl being recovered. Other reaction products, such as $CO_2$ volatilize from the reaction medium, and halides such as formed from the copper and metal from the carboxylate remain in the reaction medium.

Water should be excluded from the reaction because water tends to be reactive in the reaction system, to reduce the yield of trifluoromethylaryl. Thus, the reactants may need to be dried and water may need to be removed from the aprotic polar solvent, but rigorous treatment to exclude water is unnecessary in order for the reaction to be essentially anyhdrous. Yields in excess of 80% are obtainable by the process of the present invention, using the optimum conditions for a particular combination of reactants, and yields exceeding 90% are also obtainable.

The process of the present invention is capable of producing known trifluoromethylaryls in high yield. Examples of such aryls include benzotrifluoride, 4-nitrobenzotrifluoride, 2,2,2-trifluoroethylbenzene, and 1-trifluoromethylnaphthalene. Because the aryl group of the starting halide is nonreactive, it is apparent that the trifluoromethylated aryl reaction product can have a wide range of identities.

EXAMPLES

General Procedure

A 100 ml two-necked round-bottom flask equipped with a magnetic stirrer, water condenser, nitrogen bubbler and a thermometer was flame dried under nitrogen purge and charged with dried (freshly distilled from calcium hydride) N,N-dimethylformamide, trifluoromethylcarboxylate, cuprous iodide and aryl halide. The reaction mixture was heated to the desired temperature, causing all reactants to go into solution, and for the desired time accompanied by vigorous agitation. After cooling to room temperature, a known amount of hexafluorobenzene was added as an internal standard. After stirring for a short period, a small aliquot of the reaction mixture (solution) was removed, diluted in deuterated chloroform and the $^{19}$F NMR spectrum obtained. The yield of trifluoromethyl-aryl was calculated from the ratio of the $^{19}$F NMR signals the hexafluorobenzene standard and the trifluoromethylaryl. Details of experiments using this general procedure are reported in the following table.

Further details for the reactant charges to the flask in which the reaction was carried out can be determined from the specifics for Example 2 in the table, as follows: DMF—30 ml, the potassium carboxylate—1.58 g, CuI—1.41 g, and iodobenzene—1.06 g.

thereof trifluoromethylaryl.

2. The process of claim 1 wherein the reaction is carried out at a temperature of 50° C. to 200° C.

3. The process of claim 2 wherein the temperature is 80° C. to 130° C.

4. The process of claim 1 wherein at least 0.8 mole of said carboxylate is present for each mole of said halide.

5. The process of claim 4 wherein at least 0.8 mole of said cuprous iodide is present for each mole of said carboyxlate.

6. The process of claim 1 wherein said carboxylate is methyl ester.

7. The process of claim 1 wherein said carboxylate is metal salt.

8. The process of claim 1 wherein the metal of said metal salt is potassium.

9. The process of claim 1 wherein said halide is iodide.

10. The process of claim 1 wherein the halogen of said halide is directly substituted on the aromatic moiety of said aryl halide.

11. The process of claim 1 wherein the halogen of said halide is indirectly substituted on the aromatic moiety of said aryl halide.

12. The process of claim 1 wherein said carboxylate has the formula $CF_3O(CF_2O)_nCF_2COOM$ wherein n is 0 to 10 and M is $CH_3$, quaternary ammonium, or metal.

| Example | Carboxylate (mmol) | Aryl Halide (mmol) | CuI (mmol) | DMF (ml) | Reaction Time and Temp. (°C.) | Yield |
|---|---|---|---|---|---|---|
| 1 | $CF_3OCF_2CO_2CH_3$ 13.4 | Iodobenzene 19.2 | 13.6 | 20 | 80°–130° over 28 hours | 17% Benzotrifluoride (77% Ester Reacted) |
| 2 | $CF_3OCF_2CO_2K$ 7.2 | Iodobenzene 5.2 | 7.3 | 30 | 115° for 3 hours | 100% Benzotrifluoride |
| 3 | $CF_3OCF_2CO_2K$ 7.6 | 1-Bromo-4-nitrobenzene 7.4 | 7.5 | 30 | 115° for 3 hours | 25% 4-Nitrobenzotrifluoride |
| 4 | $CF_3OCF_2CO_2K$ 7.3 | Benzyl Bromide 7.2 | 7.6 | 30 | 115° for 3 hours | 45% (2,2,2-trifluoroethyl)benzene |
| 5 | $CF_3OCF_2OCF_2CO_2K$ 4.6 | Iodobenzene 4.5 | 4.6 | 20 | 114° for 4 hours | 73% Benzotrifluoride |
| 6 | $CF_3OCF_2CO_2Na$ 13.4 | Iodobenzene 9.8 | 14.8 | 30 | 120° for 1.75 hour | 27% Benzotrifluoride |
| 7 | $CF_3OCF_2CO_2K$ 4.8 | 1-Iodonaphthalene 4.6 | 4.9 | 30 | 115° for 3 hours | 97% 1-Trifluoromethylnaphthalene |
| 8 | $CF_3OCF_2CO_2K$ 2.4 | 1-Iodo-4-nitrobenzene 2.2 | 2.6 | 20 | 115° for 3 hours | 86% 4-Nitro-benzotrifluoride |

What is claimed is:

1. Trifluoromethylation process consisting essentially of contacting and reacting aryl halide selected from the group consisting of aryl iodide and aryl bromide with perfluoromethoxycarboxylate in the presence of cuprous iodide in an inert aprotic polar solvent and obtaining as a result

* * * * *